US012144881B2

(12) United States Patent
Wang et al.

(10) Patent No.: US 12,144,881 B2
(45) Date of Patent: Nov. 19, 2024

(54) COSMETIC COMPOSITION CONTAINING α-MANGOSTIN, METHOD FOR PREPARATION, AND USES THEREOF

(71) Applicant: CHINA PHARMACEUTICAL UNIVERSITY, Nanjing (CN)

(72) Inventors: Jinxin Wang, Nanjing (CN); Tingting Zhang, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 1032 days.

(21) Appl. No.: 17/057,627

(22) PCT Filed: Jun. 24, 2019

(86) PCT No.: PCT/CN2019/092545
§ 371 (c)(1),
(2) Date: May 12, 2021

(87) PCT Pub. No.: WO2019/223810
PCT Pub. Date: Nov. 28, 2019

(65) Prior Publication Data
US 2021/0290510 A1    Sep. 23, 2021

(30) Foreign Application Priority Data

May 21, 2018  (CN) .......................... 201810486482.4

(51) Int. Cl.
| | | |
|---|---|---|
| *A61K 8/49* | (2006.01) | |
| *A61K 8/27* | (2006.01) | |
| *A61K 8/29* | (2006.01) | |
| *A61K 8/35* | (2006.01) | |
| *A61K 8/37* | (2006.01) | |
| *A61K 8/40* | (2006.01) | |
| *A61Q 17/04* | (2006.01) | |
| *A61Q 19/02* | (2006.01) | |
| *A61Q 19/08* | (2006.01) | |

(52) U.S. Cl.
CPC .............. *A61K 8/498* (2013.01); *A61Q 17/04* (2013.01); *A61Q 19/08* (2013.01); *A61K 8/27* (2013.01); *A61K 8/29* (2013.01); *A61K 2800/522* (2013.01); *A61K 2800/591* (2013.01)

(58) Field of Classification Search
CPC ........ A61K 2800/522; A61K 2800/591; A61K 8/27; A61K 8/29; A61K 8/498; A61K 8/35; A61K 8/37; A61K 8/40; A61Q 17/04; A61Q 19/08; A61Q 19/02
See application file for complete search history.

(56) References Cited

U.S. PATENT DOCUMENTS

| | | | | |
|---|---|---|---|---|
| 2006/0105069 A1* | 5/2006 | Moffett | .............. | A61K 31/7024 424/769 |
| 2006/0210496 A1* | 9/2006 | Mower | ................ | A61K 8/9711 424/70.13 |

FOREIGN PATENT DOCUMENTS

| | | | | |
|---|---|---|---|---|
| CN | 103356442 A | | 10/2013 | |
| CN | 105130945 A | * | 9/2015 | ............. A41D 13/00 |
| CN | 106554341 A | | 4/2017 | |
| CN | 108553332 A | | 9/2018 | |
| FR | 2754447 A1 | | 4/1998 | |
| JP | 2007153773 A | * | 6/2007 | ........... A61K 31/352 |
| WO | 2017052155 A1 | | 3/2017 | |

OTHER PUBLICATIONS

PubChem CID 5281650 for Mangostin; National Library of Medicine; downloaded Nov. 28, 2023.*
Liandhajani et al.; JAPS; vol. 3 (06), pp. 070-073, published online Jun. 27, 2013.*
Berohn, Katie; 15 Best Natural and Organic Sunscreens, Tested by Skin Scientists; Good Housekeeping; update published Mar. 31, 2023.*
Zhang Chengzhong, et al., Study on ultraviolet-screening effect of extracts from mangosteen (*Garcinia mangostana* Linn.) pericarp, Journal of Hygiene Research, 2011, pp. 505-506, vol. 40, No. 4.
Linn Liandhajani, et al., Sunscreen Activity of α-mangostin from the Pericarps of Garcinia mangostana, Journal of Applied Pharmaceutical Science, 2013, pp. 070-073, vol. 3, No. 6.

* cited by examiner

*Primary Examiner* — Jeffrey T. Palenik
(74) *Attorney, Agent, or Firm* — Bayramoglu Law Offices LLC

(57) ABSTRACT

A cosmetic composition containing α-mangostin, and use thereof are disclosed. The cosmetic composition includes α-mangostin and a sunscreen agent. The α-mangostin is a pure α-mangostin or an α-mangostin-containing extract. The sunscreen agent is an inorganic sunscreen agent or an organic sunscreen agent. Herein, the inorganic sunscreen agent is one or more selected from a group of zinc oxide and titanium dioxide. The organic sunscreen agent is a sunscreen agent having a sun protection wavelength range that can be complementary to that of the α-mangostin or a sunscreen agent that is easily decomposed or easily oxidized under UV exposure. The organic sunscreen agent is one or more selected from a group of butyl methoxydibenzoylmethane, octocrilene, ethylhexyl salicylate, octyl salicylate, homosalate, ethylhexyl methoxycinnamate and terephthalylidene dicamphor sulfonic acid.

7 Claims, 2 Drawing Sheets

COSMETIC COMPOSITION CONTAINING α-MANGOSTIN, METHOD FOR PREPARATION, AND USES THEREOF

CROSS REFERENCE TO THE RELATED APPLICATIONS

This application is the national phase entry of International Application No. PCT/CN2019/092545, filed on Jun. 24, 2019, which is based upon and claims priority to Chinese Patent Application No. 201810486482.4, filed on May 21, 2018, the entire contents of which are incorporated herein by reference.

TECHNICAL FIELD

The present invention relates to a cosmetic composition, and particularly to a sunscreen or whitening cosmetic composition, and belongs to the technical field of cosmetics.

BACKGROUND

It is well known that excessive UV exposure may damage the human immune system and accelerate skin aging, leading to the development of various skin diseases and even skin cancer. UV exposure is one of the main factors that cause skin aging, and according to the wavelength range, UV rays can be divided into UVC (100-290 nm), UVB (290-320 nm), and UVA (320-400 nm) regions. UVC can be completely absorbed by the ozone layer. UVB has a high energy and is mostly absorbed by the dermis, and will cause erythema, inflammation, skin aging and even skin cancer in the case of long exposure. Although UVA has a low energy, the energy of UVA reaching the human body accounts for 98% or more of the total energy of the UV rays, and UVA has a slow effect on the skin, and although it does not cause acute inflammation, UVA may cause skin aging and serious injury under long-term effects.

Currently, sunscreen agents in sunscreen cosmetics available on the market are mainly classified into two general categories: inorganic sunscreen agents (physical UV screening agents) and organic sunscreen agents (chemical UV absorbers).

Inorganic sunscreen agents mainly include nanoscale titanium dioxide ($TiO_2$) and zinc oxide (ZnO), which protect the skin in a manner of physical blocking by reflecting or scattering the UV rays in sunlight through inorganic particles. Although inorganic sunscreen agents are relatively safe, they still have the risk of skin irritation and phototoxicity. Moreover, a relatively large amount of inorganic sunscreen agents render a heavy feel in use, which is unfavorable to skin metabolism and even causes skin diseases.

Organic sunscreen agents are divided into absorbers in the UVA range (320-400 nm) and UVB range (290-320 nm). The sunscreen principle of such UV absorbers is that electrons at the ground state absorb photons and then transit to the excited state through the transition of electronic energy level, and then release energy in various ways such as emitting fluorescence, releasing heat energy or emitting phosphorescence, and finally return to the ground state, and in such a cyclical way, the function of resisting UV rays is achieved. Such sunscreen agents have characteristics of high transparency and good absorption effects, but they cause a certain irritation to the skin and may cause side effects such as inflammation and allergies, and may interfere with endocrine in severe cases, and have genetic toxicity or reproductive toxicity and the like. In addition, organic sunscreen agents suffer from the photoinstability problem. For example, butyl methoxydibenzoylmethane suffers from the serious photoinstability problem.

Taking a wide view of the global market of sunscreen products, the development trend of sunscreen agents focuses on the following aspects: 1) full-spectrum protection has become the primary target of sunscreen products; 2) the sun protection factor (SPF) tends to increase, and the higher the SPF value, the greater the amount of the UV absorber added; 3) natural sunscreen agents have become a research hotspot: such sunscreen agents have anti-UV effects, and can eliminate sun damages such as redness and swelling, and pigmentation of the skin due to exposure to the blazing sun for quite a long time, and eliminate the side effects produced by the organic sunscreen agents, the natural sunscreen agents have advantages such as mild sun protection and high safety, but they generally have a relatively low UV absorption capacity, a narrow UV absorption band, and a relatively low broad-spectrum sunscreen capacity; and 4) combined sunscreen agents have become the main development trend: the combination of natural sunscreen agents and organic or inorganic sunscreen agents can reduce the amount of original sunscreen agents to be used, improve the skin safety, and prevent side effects on the skin caused by the organic or inorganic sunscreen agents, etc.

In summary, the current sunscreen agents commonly used in the market suffer from various drawbacks and shortcomings. There is a severe lack in novel sunscreen agents, and their development is relatively slow. Moreover, new technologies still have safety issues, and the current market demand is far from being met.

Therefore, it is extremely urgent to research and develop a safe and non-irritating sunscreen agent with good efficacy and feel in use.

SUMMARY

Technical problem to be solved: The technical problem to be solved by the present invention is to overcome the respective shortcomings of conventional inorganic sunscreen agents and organic sunscreen agents. By combining natural sunscreen agents with organic or inorganic sunscreen agents, the amount of the existing sunscreen agents to be used is reduced, to improve the skin safety, and prevent the side effects on the skin caused by the organic or inorganic sunscreen agents, and the like, while full-spectrum protection is achieved, and the sun protection effect of the product is improved.

The sun protection effects of the inorganic and organic sunscreen agents are enhanced.

The inventors of the present invention have found out that the fruit of mangosteen (Garcinia mangostana Linn.) as known as "Queen of Fruits," which is a typical tropical fruit that is native to the Malay Peninsula and the Malay Archipelago, and is cultivated more in Southeast Asia areas such as Malaysia, Thailand, the Philippines and Burma, and is also planted in Guangdong and Hainan areas of China, contains a variety of xanthone compounds and has many pharmacological activities such as anti-oxidant, anti-cancer, anti-microbial, anti-malarial, anti-viral, neuroprotective, and hypoglycemic properties. It has been proven that when α-mangostin is used in cosmetics, the sun protection effect of the cosmetics can be enhanced.

In addition, the extracted α-mangostin has poor solubility in water and cannot be highly dispersed throughout the formulation, and it will render a grainy feel when applied to the skin. Through research, the inventors of the present invention have prepared a cosmetic composition containing α-mangostin, e.g., a sunscreen composition containing α-mangostin, which is highly soluble, highly dispersible, fine and smooth, and provides a good feel in use.

Technical Solutions

To achieve the above objective, the present invention provides a cosmetic composition containing α-mangostin and a sunscreen agent.

As an embodiment of the present invention, the α-mangostin may be a pure α-mangostin or an α-mangostin-containing extract.

As another embodiment of the present invention, the sunscreen agent may be an inorganic sunscreen agent or an organic sunscreen agent.

Herein, the inorganic sunscreen agent may be one or more selected from a group of zinc oxide and titanium dioxide.

Herein, the organic sunscreen agent is a sunscreen agent having a sun protection wavelength range that can be complementary to that of the α-mangostin or a sunscreen agent that is easily decomposed or easily oxidized under UV exposure. The combination of the α-mangostin with these sunscreen agents can expand the sun protection wavelength range, and improve the photostability or oxidation stability.

Herein, the organic sunscreen agent may be one or more selected from a group of butyl methoxydibenzoylmethane, octocrilene, ethylhexyl salicylate, octyl salicylate, homosalate, ethylhexyl methoxycinnamate and terephthalylidene dicamphor sulfonic acid.

As a further embodiment of the present invention, the cosmetic composition may further comprise an oil phase, an aqueous phase, a gel phase, a sterilization preservative, and a solvent for dissolving a mixture of the α-mangostin and the sterilization preservative.

Herein, the oil phase may be one or more selected from a group of vaseline, lanolin, stearic acid and liquid paraffin.

Herein, the aqueous phase may be one or more selected from a group of SE-11, glycerin, triethanolamine and water.

Herein, the gel phase may be one or more selected from a group of Carbomer 980 and water.

Herein, the solvent may be ethanol.

Herein, the sterilization preservative may be methyl paraben.

As still another embodiment of the present invention, the cosmetic composition may comprise 0.18-5.99% of the α-mangostin based on the total weight of the composition.

The cosmetic composition provided by the present invention can achieve sun protection effects of preventing such as skin darkening, erythema, inflammation, skin aging, and even skin cancer under UV exposure.

The cosmetic composition provided by the present invention may be formulated into dosage forms such as ointments, lotions, creams, oils, gels, and sprays.

The cosmetic composition provided by the present invention can be prepared by the following method:
  preparing the oil phase, the aqueous phase and the gel phase separately;
  dissolving the α-mangostin and the sterilization preservative into the solvent to prepare a mixed solution of the α-mangostin and the sterilization preservative;
  heating the oil phase and the aqueous phase simultaneously to a temperature at which the oil phase is completely melted;
  adding the aqueous phase into the oil phase at the same temperature, followed by continuous triturating, and ceasing the heating;
  after triturating to a temperature near room temperature, adding the gel phase thereto; and
  continuing to heat, adding the mixed solution of the α-mangostin and the sterilization preservative, followed by triturating to homogeneity, to obtain the cosmetic composition.

Further, the present invention also provides a use of α-mangostin in sunscreen synergism.

Further, the present invention also provides a method for sun protection of skin, which may comprise applying the cosmetic composition comprising the α-mangostin and the sunscreen agent onto the skin.

Beneficial Effects:

(1) The α-mangostin of the present invention can be functionally complementary to the physical or chemical sunscreen agents to enhance the UVB protection effect and increase the SPF value, i.e., to enhance the effect of preventing skin darkening under UVB exposure;

(2) The α-mangostin of the present invention can inhibit the isomerization and decomposition of certain sunscreen agents, and enhance their photostability, to enhance the UVA protection effect and increase the PFA value, i.e., to enhance the effect of preventing skin aging under UVA exposure;

(3) The α-mangostin of the present invention is a natural compound, which has advantages of being safe to use, non-toxic and non-irritating to the skin, and non-teratogenic, etc.; and (4) The cosmetic composition provided by the present invention has high solubility, high dispersibility, fineness and smoothness, and good feel in use, and exhibits no obvious heavy feel, and no influence on aesthetics and skin metabolism.

DETAILED DESCRIPTION OF THE EMBODIMENTS

Figure 1:
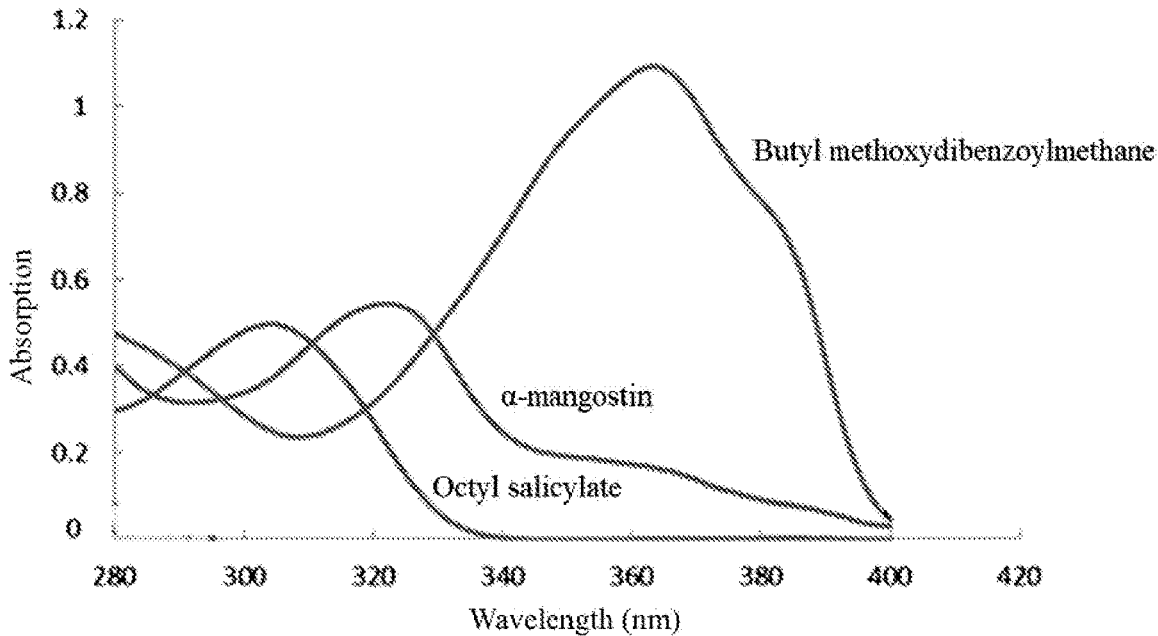
FIG. 1 shows UV absorption spectra of different compounds (α-mangostin, butyl methoxydibenzoylmethane and octyl salicylate).

The present invention will be further described below in conjunction with examples. The examples are provided to better describe the content of the present invention, but they do not limit the content of the present invention. Therefore, non-substantial improvements and adjustments can be made by those of skill in the art to the embodiments based on the above content of the present invention, and such non-substantial improvements and adjustments still fall within the protection scope of the present invention.

The α-mangostin contained in the composition of the present invention has the following chemical structure I, which may be synthetic or a commercially available product, or may be manufactured by appropriately selecting an extraction method and an extraction solvent commonly known in pharmaceutical or food companies without limitation. The conventional extraction methods may include but are not limited to ultrasonic extraction, filtration, reflux extraction, and the like.

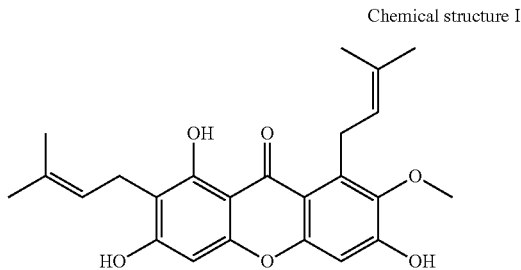 [SMILES: COc1c(O)cc2oc3cc(O)c(CC=C(C)C)c(O)c3c(=O)c2c1CC=C(C)C]

Chemical structure I

Example 1

This example is control sample 1 whose components are shown in Table 1 below:

TABLE 1

|  | Component | Weight/g |
|---|---|---|
| Oil phase | Vaseline | 1 |
|  | Lanolin | 0.5 |
|  | Stearic acid | 0.5 |
|  | Liquid paraffin | 1 |
| Aqueous phase | SE-11 | 0.1 |
|  | Glycerin | 1 |
|  | Water | 2.5 |
| Gel phase | Carbomer 980 | 0.02 |
|  | Water | 2.6 |
| Others | Ethanol | 0.5 |
|  | α-mangostin | 0.2 |
|  | Methyl paraben | 0.01 |

Preparation process: According to the amounts shown in Table 1, vaseline, lanolin, stearic acid and liquid paraffin were weighed separately and mixed to obtain an oil phase. SE-11, glycerin and water were weighed and mixed uniformly to obtain an aqueous phase. Carbomer 980 was weighed, and slowly added to water under high-speed stirring to be completely dissolved, obtaining a gel phase. The α-mangostin and methyl paraben were weighed and mixed to form a mixture, and the mixture was dissolved in ethanol to form a solution.

The oil phase and the aqueous phase were heated simultaneously to the temperature at which the oil phase was completely melted (around 80° C.). The aqueous phase was added to the oil phase at the same temperature and triturated continuously, and the heating was ceased. After triturating to the temperature near room temperature, the gel phase was added thereto, and the triturating was continued. The solution of α-mangostin and methyl paraben dissolved in ethanol was added, and triturated to homogeneity, obtaining the light yellow control sample 1.

Example 2

This example is sample 2 in one of the embodiments of the present invention whose components are shown in Table 2 below:

TABLE 2

|  | Component | Weight/g |
|---|---|---|
| Oil phase | Vaseline | 1 |
|  | Lanolin | 0.5 |
|  | Stearic acid | 0.5 |
|  | Liquid paraffin | 1 |
| Aqueous phase | SE-11 | 0.1 |
|  | Glycerin | 1 |
|  | Water | 2.5 |
| Gel phase | Carbomer 980 | 0.02 |
|  | Water | 2.6 |
| Others | Ethanol | 0.5 |
|  | α-mangostin | 0.2 |
|  | Methyl paraben | 0.01 |
|  | Zinc oxide | 0.3 |
|  | Titanium dioxide | 0.1 |

Preparation process: according to the amounts shown in Table 2, vaseline, lanolin, stearic acid and liquid paraffin were weighed separately and mixed to obtain an oil phase. SE-11, glycerin and water were weighed and mixed uniformly to obtain an aqueous phase. Carbomer 980 was weighed, and slowly added to water under high-speed stirring to be completely dissolved, obtaining a gel phase. The α-mangostin and methyl paraben were weighed and mixed to form a mixture, and the mixture was dissolved in ethanol to form a solution.

The oil phase and the aqueous phase were heated simultaneously to the temperature at which the oil phase was completely melted (around 80° C.). The aqueous phase was added to the oil phase at the same temperature and triturated continuously, and the heating was ceased. After triturating to the temperature near room temperature, the gel phase was added thereto, and the triturating was continued. The solution of α-mangostin and methyl paraben dissolved in ethanol was added, and triturated to homogeneity. Finally, zinc oxide and titanium dioxide were added thereto, and triturated again to homogeneity, obtaining the light yellow sample 2, in which the content (based on the total mass of the sample) of α-mangostin was 1.94%.

Example 3

This example is sample 3, which does not contain α-mangostin as compared with Example 2 and whose components are shown in Table 3 below:

TABLE 3

|  | Component | Weight/g |
|---|---|---|
| Oil phase | Vaseline | 1 |
|  | Lanolin | 0.5 |
|  | Stearic acid | 0.5 |
|  | Liquid paraffin | 1 |
| Aqueous phase | SE-11 | 0.1 |
|  | Glycerin | 1 |
|  | Water | 2.5 |
| Gel phase | Carbomer 980 | 0.02 |
|  | Water | 2.6 |
| Others | Ethanol | 0.5 |
|  | Methyl paraben | 0.01 |
|  | Zinc oxide | 0.3 |
|  | Titanium dioxide | 0.1 |

Preparation process: according to the amounts shown in Table 3, vaseline, lanolin, stearic acid and liquid paraffin were weighed separately and mixed to obtain an oil phase. SE-11, glycerin and water were weighed and mixed uniformly to obtain an aqueous phase. Carbomer 980 was weighed, and slowly added to water under high-speed stirring to be completely dissolved, obtaining a gel phase. Methyl paraben was weighed and dissolved in ethanol to form a solution.

The oil phase and the aqueous phase were heated simultaneously to the temperature at which the oil phase was completely melted (around 80° C.). The aqueous phase was added to the oil phase at the same temperature and triturated continuously, and the heating was ceased. After triturating to the temperature near room temperature, the gel phase was added thereto, and the triturating was continued. The solution of methyl paraben dissolved in ethanol was added, and triturated to homogeneity. Finally, zinc oxide and titanium dioxide were added thereto, and triturated again to homogeneity, obtaining the milky white sample 3.

Example 4

This example is sample 4 in one of the embodiments of the present invention whose components are shown in Table 4 below:

TABLE 4

| | Component | Weight/g |
|---|---|---|
| Oil phase | Vaseline | 1 |
| | Lanolin | 0.5 |
| | Stearic acid | 0.5 |
| | Liquid paraffin | 1 |
| Aqueous phase | SE-11 | 0.1 |
| | Glycerin | 1 |
| | Water | 2.5 |
| Gel phase | Carbomer 980 | 0.02 |
| | Water | 2.6 |
| Others | Ethanol | 0.5 |
| | α-mangostin | 0.2 |
| | Methyl paraben | 0.01 |
| | Butyl methoxydibenzoylmethane | 0.3 |
| | Octyl salicylate | 0.3 |
| | Octocrilene | 0.5 |

Preparation process: according to the amounts shown in Table 4, vaseline, lanolin, stearic acid and liquid paraffin were weighed separately and mixed, and also butyl methoxydibenzoylmethane, octyl salicylate and octocrilene were added thereto, to obtain an oil phase. SE-11, glycerin and water were weighed and mixed uniformly to obtain an aqueous phase, Carbomer 980 was weighed, and slowly added to water under high-speed stirring to be completely dissolved, obtaining a gel phase. The α-mangostin and methyl paraben were weighed and mixed to form a mixture, and the mixture was dissolved in ethanol to form a solution.

The oil phase and the aqueous phase were heated simultaneously to the temperature at which the oil phase was completely melted (around 80° C.). The aqueous phase was added to the oil phase at the same temperature and triturated continuously, and the heating was ceased. After triturating to the temperature near room temperature, the gel phase was added thereto, and the triturating was continued. The solution of α-mangostin and methyl paraben dissolved in ethanol was added, and triturated to homogeneity, obtaining the light yellow sample 4, in which the content (based on the total mass of the sample) of α-mangostin was 1.81%.

Example 5

This example is sample 5, which does not contain α-mangostin as compared with Example 4 and whose components are shown in Table 5 below:

TABLE 5

| | Component | Weight/g |
|---|---|---|
| Oil phase | Vaseline | 1 |
| | Lanolin | 0.5 |
| | Stearic acid | 0.5 |
| | Liquid paraffin | 1 |
| Aqueous phase | SE-11 | 0.1 |
| | Glycerin | 1 |
| | Water | 2.5 |
| Gel phase | Carbomer 980 | 0.02 |
| | Water | 2.6 |
| Others | Ethanol | 0.5 |
| | Methyl paraben | 0.01 |
| | Butyl methoxydibenzoylmethane | 0.3 |
| | Octyl salicylate | 0.3 |
| | Octocrilene | 0.5 |

Preparation process: according to the amounts shown in Table 5, vaseline, lanolin, stearic acid and liquid paraffin were weighed separately and mixed, and also butyl methoxydibenzoylmethane, octyl salicylate and octocrilene were added thereto, to obtain an oil phase. SE-11, glycerin and water were weighed and mixed uniformly to obtain an aqueous phase. Carbomer 980 was weighed, and slowly added to water under high-speed stirring to be completely dissolved, obtaining a gel phase. Methyl paraben was weighed and dissolved in ethanol to form a solution.

The oil phase and the aqueous phase were heated simultaneously to the temperature at which the oil phase was completely melted (around 80° C.). The aqueous phase was added to the oil phase at the same temperature and triturated continuously, and the heating was ceased. After triturating to the temperature near room temperature, the gel phase was added thereto, and the triturating was continued. The solution of methyl paraben dissolved in ethanol was added, and triturated to homogeneity, obtaining the milky white sample 5.

Example 6

This example is sample 6 in one of the embodiments of the present invention, whose components are shown in Table 6 below:

TABLE 6

| | Component | Weight/g |
|---|---|---|
| Oil phase | Vaseline | 1 |
| | Lanolin | 0.5 |
| | Stearic acid | 0.5 |
| | Liquid paraffin | 1 |
| Aqueous phase | SE-11 | 0.1 |
| | Glycerin | 1 |
| | Water | 2.5 |
| Gel phase | Carbomer 980 | 0.02 |
| | Water | 2.6 |
| Others | Ethanol | 0.5 |
| | α-mangostin | 0.02 |
| | Methyl paraben | 0.01 |
| | Butyl methoxydibenzoylmethane | 0.3 |
| | Octyl salicylate | 0.3 |
| | Octocrilene | 0.5 |

Preparation process: according to the amounts shown in Table 6, vaseline, lanolin, stearic acid and liquid paraffin were weighed separately and mixed, and also butyl methoxydibenzoylmethane, octyl salicylate and octocrilene were added thereto, to obtain an oil phase. SE-11, glycerin and water were weighed and mixed uniformly to obtain an aqueous phase. Carbomer 980 was weighed, and slowly added to water under high-speed stirring to be completely dissolved, obtaining a gel phase. The α-mangostin and methyl paraben were weighed and mixed to form a mixture, and the mixture was dissolved in ethanol to form a solution.

The oil phase and the aqueous phase were heated simultaneously to the temperature at which the oil phase was completely melted (around 80° C.). The aqueous phase was added to the oil phase at the same temperature and triturated continuously, and the heating was ceased. After triturating to the temperature near room temperature, the gel phase was added thereto, and the triturating was continued. The solution of α-mangostin and methyl paraben dissolved in ethanol was added, and triturated to homogeneity, obtaining the light yellow sample 6, in which the content (based on the total mass of the sample) of α-mangostin was 0.18%.

Example 7

This example is sample 7 in one of the embodiments of the present invention, whose components are shown in Table 7 below:

TABLE 7

| | Component | Weight/g |
|---|---|---|
| Oil phase | Vaseline | 1 |
| | Lanolin | 0.5 |
| | Stearic acid | 0.5 |
| | Liquid paraffin | 1 |
| Aqueous phase | SE-11 | 0.1 |
| | Glycerin | 1 |
| | Water | 2.5 |
| Gel phase | Carbomer 980 | 0.02 |
| | Water | 2.6 |
| Others | Ethanol | 0.5 |
| | α-mangostin | 0.69 |
| | Methyl paraben | 0.01 |
| | Butyl methoxydibenzoylmethane | 0.3 |
| | Octyl salicylate | 0.3 |
| | Octocrilene | 0.5 |

Preparation process: according to the amounts shown in Table 7, vaseline, lanolin, stearic acid and liquid paraffin were weighed separately and mixed, and also butyl methoxydibenzoylmethane, octyl salicylate and octocrilene were added thereto to obtain an oil phase. SE-11, glycerin and water were weighed and mixed uniformly to obtain an aqueous phase. Carbomer 980 was weighed, and slowly added to water under high-speed stirring to be completely dissolved, obtaining a gel phase. The α-mangostin and methyl paraben were weighed and mixed to form a mixture, and the mixture was dissolved in ethanol to form a solution.

The oil phase and the aqueous phase were heated simultaneously to the temperature at which the oil phase was completely melted (around 80° C.). The aqueous phase was added to the oil phase at the same temperature and triturated continuously, and the heating was ceased. After triturating to the temperature near room temperature, the gel phase was added thereto, and the triturating was continued. The solution of α-mangostin and methyl paraben dissolved in ethanol was added, and triturated to homogeneity, obtaining the light yellow sample 7, in which the content (based on the total mass of the sample) of α-mangostin was 5.99%.

Example 8

In order to verify the sun protection effect of α-mangostin in the cosmetic compositions, SPF values and PFA values of samples 1-7 from Examples 1-7 were tested in the present invention.

Experimental materials: standard for detection of the SPF value and PFA value, commercially available from Cosmetech Laboratories Inc.; PMMA (methyl methacrylate) plates; UV 2000S UV transmittance analyzer from Lab sphere Corporation; and SOL-UV-6 solar simulator from Newport Corporation.

Detection method: Using the ISO 24443:2012 standard and a dose of 1.3 mg/cm$^2$, a predetermined volume of each of the test samples or the standard was drawn with a special syringe and uniformly spotted on the surface of a PMMA plate, and spread with a medical latex finger cot to allow it to be distributed uniformly on the surface of the PMMA plate. The whole plate was placed in an environment with room temperature of 23-26° C. and a relative humidity of 40-60%, and protected from light for 30 min. Then, the UV 2000S instrument was used to detect the UV transmittance, with 4 replicate test plates for each sample and 5 points detected for each plate, and the SPF values of the standard and the samples were recorded separately. After the test, the sample-applied PMMA plates were placed under the SOL-UV-6 solar simulator for exposure, and then the UV 2000S instrument was used to detect the UV transmittance again, with 4 replicate test plates for each sample and 5 points detected for each plate, and the PFA values of the standard and the samples were recorded separately.

Results are shown in Tables 8-9 below:

TABLE 8

| | SPF values | | | | |
|---|---|---|---|---|---|
| | Measured value 1 | Measured value 1 | Measured value 1 | Measured value 1 | Mean |
| Sample 1 | 1.74 | 1.85 | 1.78 | 1.75 | 1.76 ± 0.05 |
| Sample 2 | 8.43 | 9.99 | 8.58 | 11.15 | 9.82 ± 1.06 |
| Sample 3 | 4.89 | 5.11 | 5.16 | 4.92 | 4.54 ± 0.59 |
| Sample 4 | 33.45 | 32.45 | 34.54 | 34.75 | 34.40 ± 1.98 |
| Sample 5 | 15.30 | 16.53 | 14.36 | 17.57 | 16.07 ± 1.78 |
| Sample 6 | 19.62 | 18.26 | 19.16 | 16.36 | 18.35 ± 0.69 |
| Sample 7 | 33.78 | 35.19 | 35.96 | 37.19 | 35.53 ± 1.28 |
| Standard | 15.83 | 14.87 | 14.64 | 14.90 | 15.06 ± 0.53 |

TABLE 9

| | PFA values | | | | |
|---|---|---|---|---|---|
| | Measured value 1 | Measured value 1 | Measured value 1 | Measured value 1 | Mean |
| Sample 1 | 1.59 | 1.61 | 1.60 | 1.60 | 1.60 ± 0.01 |
| Sample 2 | 5.46 | 5.05 | 5.95 | 5.32 | 5.45 ± 0.38 |
| Sample 3 | 3.26 | 3.48 | 3.05 | 3.20 | 3.25 ± 0.18 |
| Sample 4 | 14.27 | 15.50 | 13.50 | 13.28 | 14.14 ± 1.00 |

TABLE 9-continued

| | PFA values | | | | |
|---|---|---|---|---|---|
| | Measured value 1 | Measured value 1 | Measured value 1 | Measured value 1 | Mean |
| Sample 5 | 13.12 | 12.19 | 12.06 | 13.56 | 12.98 ± 0.65 |
| Sample 6 | 12.94 | 13.48 | 12.76 | 13.82 | 13.25 ± 0.42 |
| Sample 7 | 14.39 | 14.83 | 15.25 | 13.65 | 14.53 ± 0.28 |
| Standard | 13.65 | 12.21 | 13.40 | 11.72 | 12.75 ± 0.93 |

As shown in Tables 8-9 above, the SPF value and PFA value of sample 4 are significantly higher than those of the other examples, and are much higher than those of the standard. Specifically, both SPF value and PFA value of sample 1 (Example 1) are very low, indicating that although the α-mangostin has anti-UV absorption capacity, it has very weak UVA and UVB protection effects when used alone.

Sample 2 (Example 2) and sample 3 (Example 3) both have the same amount of the physical sunscreen agent added, but sample 2 has the α-mangostin added. The results show that both the SPF value and PFA value of sample 2 are significantly higher than those of sample 3, indicating that the combination of the α-mangostin and the physical sunscreen agent can significantly improve the UVA and UVB protection effects of the physical sunscreen agent.

Further, sample 4 (Example 4) and sample 5 (Example 5) both have the same amount of the chemical sunscreen agent added, but sample 4 has the α-mangostin added. The results show that both the SPF value and PFA value of sample 4 are significantly higher than those of sample 5, indicating that the combination of the α-mangostin and the chemical sunscreen agent can significantly improve the UVA and UVB protection effects of the chemical sunscreen agent.

The content of α-mangostin (based on the total mass of the sample) in sample 6 (Example 6) is only 0.18%. The results show that both the SPF value and PFA value of sample 6 are higher than those of sample 5, indicating that the combination of the α-mangostin at a low content and the chemical sunscreen agent can improve the UVA and UVB protection effects of the chemical sunscreen agent to a certain extent.

The content of α-mangostin (based on the total mass of the sample) in sample 7 (Example 7) is 5.99%. The results show that both the SPF value and PFA value of sample 7 are significantly higher than those of sample 5, indicating that the combination of the α-mangostin at a high content and the chemical sunscreen agent can significantly improve the UVA and UVB protection effects of the chemical sunscreen agent.

It is confirmed in the above that the α-mangostin has the effect of enhancing the UVA and UVB protection effects of physical sunscreen agents and chemical sunscreen agents, providing the sunscreen synergism.

Example 9

In order to verify the sun protection effect of the cosmetic composition containing α-mangostin on the human body, the SPF values and PFA values of samples 1, 4 and 5 applied on the human body were tested separately in the present invention.

Test materials: samples 1, 4 and 5; standard control: SPF value 4.4±0.4, formulated according to the ISO 24444 (2010) standard formula.

Test Method:
(6) Before the test, the subjects each were provided with the test instructions and signed an informed consent.
(7) The subjects who participated in the test were screened into groups according to the test requirements, with 10 subjects for each sample.
(8) The subjects leaned forward and were subjected to UV exposure on their backs. 24 h before the test, the minimal erythema dose (MEDu') of the subjects' skin to the UV exposure should be predetermined, and the UV exposure dose should be adjusted based on the predetermined results, for detection of the samples. On the test day, first a normal skin area larger than 50 cm$^2$ was selected on the back of each subject, and the samples to be tested or the standard control each were applied uniformly on the area in an amount of (2.00±0.05) mg/cm$^2$ of each of the samples.
(9) Then the appropriate UV exposure doses were selected, and the UV exposure was performed in the following 3 situations:
   a) In the test area with no sample applied, the UV exposure dose was adjusted, MEDu of the subjects' unprotected skin was determined again, wherein 6 test points corresponding to 6 optical fibers were exposed to increasing UV doses.
   b) In the test area protected by each of the samples to be tested, the expected SPF of the test product was multiplied by the predetermined MEDu' of the subject to obtain a time value which should be the median of the UV exposure doses, wherein 6 test points were exposed to increasing UV doses.
   c) In the test area protected by the standard control, the expected SPF of the standard control was multiplied by the predetermined MEDu' of the subject to obtain a time value which should be the median of the UV exposure doses, wherein 6 test points were exposed to increasing UV doses.
(10) 24 h later, the test results were observed, the MED was visually evaluated, and judged by an observer under sufficient and uniform lighting conditions, and MED values in the 4 situations were recorded separately.

Method for Calculating the SPF Value:

The SPFi value of each of the samples to be tested or the standard to protect a single subject was expressed by the following formula:

$$SPFi = \frac{MED \text{ of skin protected by the test sample/standard}}{MED \text{ of unprotected skin}}$$

Test results: Tables 10-12 show the SPF values of samples 1, 4, and 5 from the above examples applied respectively on human skin after 24 h of UV exposure.

TABLE 10

| Group No. | MED unprotected 24 h before | MED unprotected 24 h later | Standard Dose mg/cm$^2$ | Standard MED | Standard SPFi | Test sample (sample 1) Dose mg/cm$^2$ | Test sample (sample 1) MED | Test sample (sample 1) SPFi |
|---|---|---|---|---|---|---|---|---|
| 1 | 95.32 | 186.16 | 2.00 | 595.75 | 3.2 | 2.05 | 244.02 | 1.3 |
| 2 | 76.25 | 95.32 | 1.98 | 381.25 | 4.0 | 1.97 | 195.20 | 2.0 |
| 3 | 96.72 | 158.39 | 2.01 | 824.10 | 5.2 | 2.04 | 291.91 | 1.8 |
| 4 | 90.61 | 169.38 | 1.97 | 474.31 | 2.8 | 2.01 | 294.59 | 1.7 |
| 5 | 86.29 | 129.47 | 2.00 | 574.85 | 4.4 | 1.99 | 213.52 | 1.6 |
| 6 | 84.87 | 178.49 | 2.02 | 731.81 | 4.1 | 1.98 | 284.37 | 1.6 |
| 7 | 79.30 | 100.64 | 1.99 | 284.83 | 2.8 | 2.02 | 185.48 | 1.8 |
| 8 | 89.29 | 152.94 | 1.98 | 474.42 | 3.1 | 2.00 | 241.13 | 1.6 |
| 9 | 93.68 | 175.28 | 1.99 | 578.42 | 3.3 | 1.97 | 338.75 | 1.9 |
| 10 | 92.89 | 181.47 | 2.00 | 640.59 | 3.5 | 2.01 | 282.00 | 1.6 |

*SPFi of the test group for the standard has a mean of 3.7, a standard deviation of 0.8, and a standard error of 0.2.
*SPFi of the test group for sample 1 has a mean of 1.7, a standard deviation of 0.2, and a standard error of 0.1.

TABLE 11

| Group No. | MED unprotected 24 h before | MED unprotected 24 h later | Standard Dose mg/cm$^2$ | Standard MED | Standard SPFi | Test sample (sample 4) Dose mg/cm$^2$ | Test sample (sample 4) MED | Test sample (sample 4) SPFi |
|---|---|---|---|---|---|---|---|---|
| 1 | 95.32 | 186.16 | 2.00 | 595.75 | 3.2 | 2.02 | 2025.55 | 10.9 |
| 2 | 76.25 | 95.32 | 1.98 | 381.25 | 4.0 | 1.98 | 2025.39 | 21.2 |
| 3 | 96.72 | 158.39 | 2.01 | 824.10 | 5.2 | 2.01 | 2140.29 | 13.5 |
| 4 | 90.61 | 169.38 | 1.97 | 474.31 | 2.8 | 1.98 | 3055.45 | 18.0 |
| 5 | 86.29 | 129.47 | 2.00 | 574.85 | 4.4 | 1.99 | 2330.47 | 18.0 |
| 6 | 84.87 | 178.49 | 2.02 | 731.81 | 4.1 | 1.98 | 2536.70 | 14.2 |
| 7 | 79.30 | 100.64 | 1.99 | 284.83 | 2.8 | 2 | 1519.75 | 15.1 |
| 8 | 89.29 | 152.94 | 1.98 | 474.42 | 3.1 | 2.02 | 2499.04 | 16.3 |
| 9 | 93.68 | 175.28 | 1.99 | 578.42 | 3.3 | 2.01 | 2979.78 | 17.0 |
| 10 | 92.89 | 181.47 | 2.00 | 640.59 | 3.5 | 1.99 | 2963.41 | 16.3 |

*SPFi of the test group for the standard has a mean of 3.7, a standard deviation of 0.8, and a standard error of 0.2.
*SPFi of the test group for sample 4 has a mean of 16.1, a standard deviation of 2.9, and a standard error of 0.9.

TABLE 12

| Group No. | MED unprotected 24 h before | MED unprotected 24 h later | Standard Dose mg/cm$^2$ | Standard MED | Standard SPFi | Test sample (sample 5) Dose mg/cm$^2$ | Test sample (sample 5) MED | Test sample (sample 5) SPFi |
|---|---|---|---|---|---|---|---|---|
| 1 | 95.32 | 186.16 | 2.00 | 595.75 | 3.2 | 2.05 | 1620.44 | 8.7 |
| 2 | 76.25 | 95.32 | 1.98 | 381.25 | 4.0 | 1.98 | 829.60 | 8.7 |
| 3 | 96.72 | 158.39 | 2.01 | 824.10 | 5.2 | 2.02 | 1395.29 | 8.8 |
| 4 | 90.61 | 169.38 | 1.97 | 474.31 | 2.8 | 2.03 | 1424.64 | 8.4 |
| 5 | 86.29 | 129.47 | 2.00 | 574.85 | 4.4 | 1.98 | 1033.20 | 8.0 |
| 6 | 84.87 | 178.49 | 2.02 | 731.81 | 4.1 | 1.99 | 1661.35 | 9.3 |
| 7 | 79.30 | 100.64 | 1.99 | 284.83 | 2.8 | 2.00 | 906.69 | 9.0 |
| 8 | 89.29 | 152.94 | 1.98 | 474.42 | 3.1 | 2.01 | 1359.68 | 8.9 |
| 9 | 93.68 | 175.28 | 1.99 | 578.42 | 3.3 | 1.97 | 1563.32 | 8.9 |
| 10 | 92.89 | 181.47 | 2.00 | 640.59 | 3.5 | 2.01 | 1540.68 | 8.5 |

*SPFi of the test group for the standard has a mean of 3.7, a standard deviation of 0.8, and a standard error of 0.2.
*SPFi of the test group for sample 5 has a mean of 8.7, a standard deviation of 0.4, and a standard error of 0.1.

The results are consistent with Example 8. The SPF value of sample 1 on human body is very low, indicating that although the α-mangostin has anti-UV absorption capacity, it has very weak UVA and UVB protection effects when used alone. Sample 4 (Example 4) and sample 5 (Example 5) both have the same amount of the chemical sunscreen agent added, but sample 4 has the α-mangostin added, and thus, after 24 h of light exposure, the SPF value of sample 4 on human body is higher than that of sample 5.

The test on human skin further confirms that the combination of the α-mangostin and chemical sunscreen agents can significantly improve the UVA and UVB protection effects of the chemical sunscreen agents, and the α-mangostin can be used well in cosmetic compositions for sunscreen synergism.

Example 10

This example reveals the complementary effect of α-mangostin on the UV absorption by butyl methoxydibenzoylmethane and octyl salicylate. The present inventors tested the UV absorbance of α-mangostin, butyl methoxydibenzoylmethane and octyl salicylate in the UV wavelength region separately. FIG. 1 shows the UV absorption spectra of different compounds.

As shown in FIG. 1, the α-mangostin has a relatively broad spectrum of UV absorption peaks, with relatively strong absorption from the UVB range of 290-320 nm to the UVA range of 320-400 nm. Therefore, the α-mangostin has obvious advantages over the sunscreen agent octyl salicylate, and has a part of the absorption band which can be complementary to that of octyl salicylate, enhancing the UVB protection effect and increasing the SPF value. At the same time, the α-mangostin can also be well complementary to butyl methoxydibenzoylmethane having relatively weak absorption intensity in the UVB range, increasing the SPF value.

Example 11

The present inventors found that the α-mangostin, as a flavonoid compound, has a conjugated structure. In addition to showing strong absorption for both UV and visible light, and being highly stable in the visible and UV regions, the α-mangostin can also absorb a part of photons that impact butyl methoxydibenzoylmethane, to prevent butyl methoxydibenzoylmethane from being inactivated from the excited state, so that butyl methoxydibenzoylmethane can maintain its original properties without losing light absorption capacity, which enhances the photostability of butyl methoxydibenzoylmethane and inhibits the photolysis of butyl methoxydibenzoylmethane.

In this example, an experiment was conducted on the inhibition of photolysis of butyl methoxydibenzoylmethane by α-mangostin, and it was confirmed that α-mangostin can inhibit the photolysis of the UVA sunscreen agent butyl methoxydibenzoylmethane, which explains why α-mangostin enhances the UVA protection effect of butyl methoxydibenzoylmethane and increases the PFA value.

Instrument and equipment: Model 751-GW spectrophotometer; and FA1004 electronic balance.

Reagents: butyl methoxydibenzoylmethane, from Shanghai SIMP Co., Ltd.; and an α-mangostin sample.

Experimental Method:

(6) Formulation of standard stock solutions of butyl methoxydibenzoylmethane and the sample: 20.0 mg of butyl methoxydibenzoylmethane and α-mangostin were weighed separately, and diluted with a specific mixed solvent (an acetone-water mixed solvent with a ratio by volume of acetone to water of 5:1, hereinafter referred to as mixed solvent) to a volume of 10 ml.

(7) Formulation of reference solutions of butyl methoxydibenzoylmethane and the sample: The mixed solvent was used as the reference solution of butyl methoxydibenzoylmethane. 0.1 ml of the standard stock solution of the α-mangostin sample was drawn, and diluted with the mixed solvent to a volume of 10 ml, as the reference solution of the sample.

(8) Formulation of standard working solutions (20 μg/ml) of butyl methoxydibenzoylmethane and the sample: 0.1 ml of the standard stock solution of butyl methoxydibenzoylmethane was drawn and diluted with the mixed solvent to a volume of 10 ml. 0.1 ml aliquots of the standard stock solution of the α-mangostin sample were drawn separately, and added separately to 0.1 ml aliquots of the standard stock solution of butyl methoxydibenzoylmethane, and then diluted with the mixed solvent to a volume of 10 ml.

(9) Reference solutions and standard working solutions of different concentrations of rutin were formulated according to Steps (2) and (3).

(10) Determination of the photolysis rate and photolysis inhibition rate of butyl methoxydibenzoylmethane: The absorbance of the standard working solution of butyl methoxydibenzoylmethane and the absorbance of butyl methoxydibenzoylmethane in the α-mangostin sample were measured at 357 nm. Then they were subjected to the sunlight exposure, and the absorbance thereof was measured every day. The photolysis rate, the photolysis inhibition rate and the M value of butyl methoxydibenzoylmethane were calculated according to the following formulas:

% Photolysis rate=$(A_0-A_i)/A_0 \times 100\%$

% Photolysis inhibition rate=$[1-(B_0-B_i)/(A_0-A_i)] \times 100$ $M=B_i/A_i$

In the formulas, $A_0$ is the absorbance of the standard working solution of butyl methoxydibenzoylmethane; $A_i$ is the absorbance of the standard working solution of butyl methoxydibenzoylmethane after i days of light exposure; $B_0$ is the absorbance of butyl methoxydibenzoylmethane in the standard working solution of the α-mangostin sample; $B_i$ is the absorbance of butyl methoxydibenzoylmethane in the standard working solution of the α-mangostin sample after i days of light exposure; and M is the ratio of the amount of butyl methoxydibenzoylmethane remaining in the α-mangostin sample to the amount of butyl methoxydibenzoylmethane remaining in the control sample without the sample added.

Figure 2:
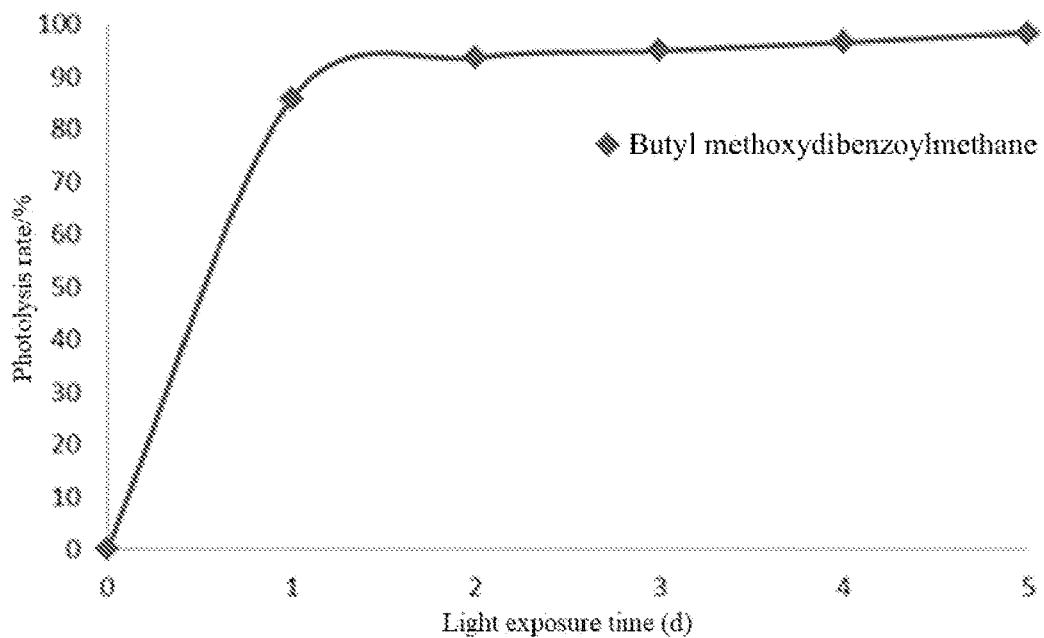
FIG. 2 is a graph of light exposure time vs. photolysis rate of butyl methoxydibenzoylmethane.
Figure 3:
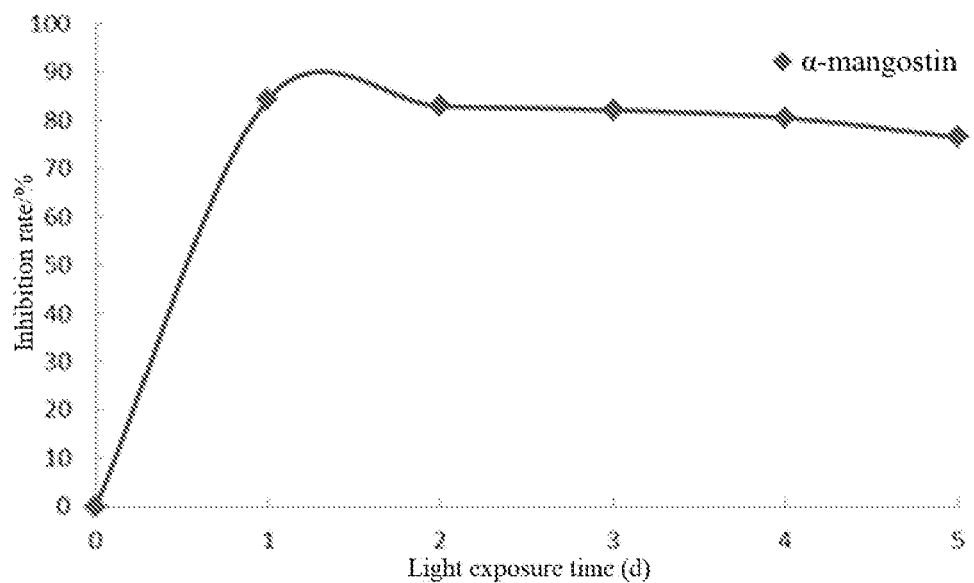
FIG. 3 is a graph of light exposure time vs. photolysis inhibition rate of an α-mangostin sample.

For the above α-mangostin sample and butyl methoxydibenzoylmethane, each was determined for the photolysis inhibition rate or the photolysis rate at the same exposure time, to obtain the curve of light exposure time vs. photolysis inhibition rate of the α-mangostin sample (FIG. 3) and the curve of light exposure time vs. photolysis rate of butyl methoxydibenzoylmethane (FIG. 2). Table 8 shows the relationship of the photolysis rate of butyl methoxydibenzoylmethane and the inhibition rate of the sample with the light exposure time. Table 13 shows the inhibition of photolysis of butyl methoxydibenzoylmethane by the α-mangostin sample.

TABLE 13

| | Light exposure time (d) | | | | |
| --- | --- | --- | --- | --- | --- |
| | 1 | 2 | 3 | 4 | 5 |
| photolysis rate of butyl methoxydibenzoylmethane/% | 85.7 | 93.7 | 95.0 | 96.6 | 98.4 |
| Inhibition rate of α-mangostin/% | 84.3 | 82.9 | 82.1 | 80.5 | 76.4 |

TABLE 14

| | Inhibition rate/% | M value | |
| --- | --- | --- | --- |
| Sample | (Day 1) | Day 1 | Day 2 |
| α-mangostin | 84.3 | 5.77 | 12.31 |

As shown in Table 13 and FIG. 2, the absorbance and concentration of butyl methoxydibenzoylmethane are basically in linear relationship. Therefore, the photolysis rate of butyl methoxydibenzoylmethane can be calculated by the formula. Under sunlight exposure, the photolysis rate of butyl methoxydibenzoylmethane in one day is as high as 85.7%, and butyl methoxydibenzoylmethane is almost completely decomposed in five continuous days. Therefore, butyl methoxydibenzoylmethane is a photo-decomposable substance. As shown in Table 14 and FIG. 3, the photolysis rate of butyl methoxydibenzoylmethane in the α-mangostin sample is significantly reduced, indicating that the α-mangostin has a very good inhibitory effect on the photolysis of butyl methoxydibenzoylmethane, thereby enhancing the UVA protection effect of butyl methoxydibenzoylmethane and increasing the PFA value of the sunscreen composition.

Antioxidant Activity Test

Test Method: Oxygen Radical Absorbance Capacity (ORAC) Assay

Specific method: An extraction solution containing a solubilizing compound was prepared, the sample was added to the extraction solution to extract the antioxidants present in the sample, and a fluorescent probe was added to the extract, a free radical generator was added to the extract, to detect the decay of the fluorescence intensity of the probe in the sample over time, and calculate the oxidation resistance of the sample based on the decay of the fluorescence intensity of the probe in the sample.

Test results:

| Analysis item | Result | Unit |
| --- | --- | --- |
| ORAC against peroxyl radicals | 8,704 | μmole TE/gram |
| ORAC against hydroxyl radicals | 9,055 | μmole TE/gram |
| ORAC against peroxynitrite | 404 | μmole TE/gram |
| ORAC against oxide anion | 13,043 | μmole TE/gram |
| ORAC against single oxygen | 262 | μmole TE/gram |
| ORAC 5.0 (sum of above) | 31,468 | μmole TE/gram |

Note: There are 5 main reactive oxygen species (ROS) in the human body: peroxy radicals, hydroxyl radicals, peroxynitrite, superoxide anions and singlet oxygen.

The results of ORAC are expressed as micromole trolox equivalent (μmole TE)/gram. Trolox is a vitamin E analog, which is an antioxidant standard substance.

The above examples are only intended for illustration, instead of limitation, of the technical solutions of the present invention. Although the present invention has been described in detail with reference to the preferred examples, it is to be understood by those of ordinary skill in the art that, modification or equivalent replacements may be made to the technical solutions of the present invention, without departing from the purpose and scope of the technical solutions of the present invention, and should be all encompassed within the scope of claims of the present invention.

What is claimed is:

1. A cosmetic composition, comprising
α-mangostin and
an organic sunscreen agent, wherein
the organic sunscreen agent has a sun protection wavelength range being complementary to a sun protection wavelength range of the α-mangostin or the organic sunscreen agent is decomposed under UV exposure;
the organic sunscreen agent consists of butyl methoxydibenzoylmethane, octyl salicylate and octocrilene; and
the content of α-mangostin is 1.81-5.99% based on a total weight of the cosmetic composition.

2. The cosmetic composition according to claim 1, wherein the α-mangostin is a pure α-mangostin or an α-mangostin-containing extract.

3. The cosmetic composition according to claim 1, wherein sun protection comprises preventing skin darkening and/or erythema, inflammation, skin aging, and a skin cancer under UV exposure.

4. The cosmetic composition according to claim 1, wherein the content of butyl methoxydibenzoylmethane is 2.60-2.72% based on a total weight of the cosmetic composition, the content of octyl salicylate is 2.60-2.72% based on a total weight of the cosmetic composition and the content of octocrilene is 4.34-4.53% based on a total weight of the cosmetic composition.

5. A method of increasing a sunscreen sun protection factor (SPF) value of an organic sunscreen agent, comprising adding α-mangostin to a cosmetic composition, wherein
the cosmetic composition comprises an organic sunscreen agent, wherein the organic sunscreen agent consists of butyl methoxydibenzoylmethane, octyl salicylate and octocrilene;
the content of α-mangostin is 1.81-5.99% based on a total weight of the cosmetic composition; and
the α-mangostin synergistically increases an SPF value of the organic sunscreen agent under UVA and UVB exposure.

6. The method of increasing a sunscreen sun protection factor (SPF) value of an organic sunscreen agent according to claim 5, wherein the content of butyl methoxydibenzoylmethane is 2.60-2.72% based on a total weight of the cosmetic composition, the content of octyl salicylate is 2.60-2.72% based on a total weight of the cosmetic composition and the content of octocrilene is 4.34-4.53% based on a total weight of the cosmetic composition.

7. A method of preparing the cosmetic composition according to claim 1 comprising the following steps:
(S1) preparing an oil phase, an aqueous phase and an gel phase separately;
(S2) dissolving the α-mangostin and a sterilization preservative into a solvent to prepare a mixed solution of the α-mangostin and the sterilization preservative;
(S3) heating the oil phase and the aqueous phase simultaneously to a temperature at which the oil phase is completely melted;
(S4) adding the aqueous phase into the oil phase at the same temperature, followed by continuous triturating, and ceasing the heating;
(S5) after triturating to a temperature near room temperature, adding the gel phase thereto; and
(S6) continuing to heat, adding the mixed solution of the α-mangostin and the sterilization preservative, followed by triturating to homogeneity, to obtain the cosmetic composition.

* * * * *